(12) United States Patent
Bedding et al.

(10) Patent No.: US 6,841,380 B2
(45) Date of Patent: Jan. 11, 2005

(54) APPARATUS FOR PROVIDING AN ENVIRONMENT OF CONTROLLED WATER ACTIVITY FOR STORAGE OF NEMATODES

(75) Inventors: Robin Anthony Bedding, Cook (AU); Simone Daniela Clark, Murrumbateman (AU); Karen Louise Butler, Queanbeyan (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 204 days.

(21) Appl. No.: 10/146,073

(22) Filed: May 16, 2002

(65) Prior Publication Data

US 2003/0017577 A1 Jan. 23, 2003

Related U.S. Application Data

(63) Continuation of application No. 09/806,143, filed as application No. PCT/AU99/00829 on Sep. 28, 1999, now Pat. No. 6,407,310.

(30) Foreign Application Priority Data

Sep. 28, 1998 (AU) .............................................. 6167/98

(51) Int. Cl.[7] .......................... C12M 1/00; C12M 3/00; C12N 5/00; C12N 15/74
(52) U.S. Cl. ............................... 435/307.1; 435/283.1; 435/325
(58) Field of Search .......................... 435/283.1, 307.1, 435/325

(56) References Cited

U.S. PATENT DOCUMENTS

| 4,765,275 A | 8/1988 | Yukawa et al. |
| 5,042,427 A | 8/1991 | Bedding |
| 5,183,950 A | 2/1993 | Popiel et al. |

FOREIGN PATENT DOCUMENTS

| WO | WO85/03412 A1 | 8/1985 |
| WO | WO89/07446 A1 | 8/1989 |
| WO | WO94/05150 A1 | 3/1994 |
| WO | WO94/19940 A1 | 9/1994 |

*Primary Examiner*—David M. Naff
*Assistant Examiner*—Deborah K. Ware
(74) *Attorney, Agent, or Firm*—Sughrue Mion, PLLC

(57) ABSTRACT

Third stage juvenile (J3) entomopathogenic nematodes are prepared for storage by being induced into a state of cryptobiosis. The induction of cryptobiosis is effected by mixing an aqueous cream of the J3 nematodes with anhydrous, small particles of non-fibrous cellulose. The cryptobiotic J3 nematodes are stored in a container, fitted with an attachment which maintains the water activity in the container at a required value. The attachment includes a rigid tube that connects the interior of the container with a chamber that is vented to ambient atmosphere by small apparatus. The chamber contains water-absorbent material saturated with water or with a saturated salt solution, and the tube contains an air-permeable plug. An alternative attachment comprises a plastic envelope as the chamber, one face of which is stuck to the wall of the container. Small aperatures in the face are aligned with apertures in the container wall. Small apertures in the other face connect the inside of the envelope to ambient atmosphere.

9 Claims, 2 Drawing Sheets

Figure 1:
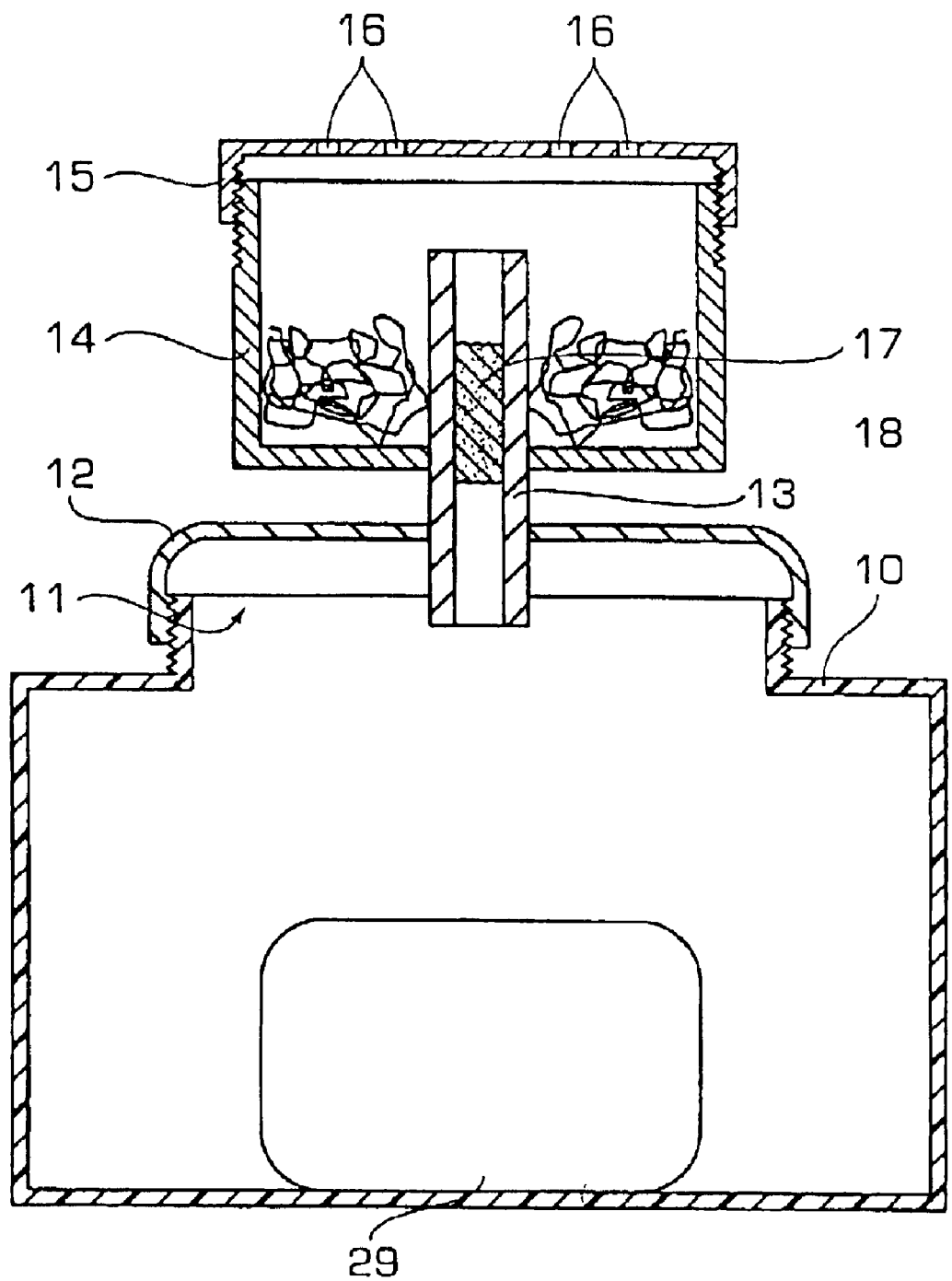

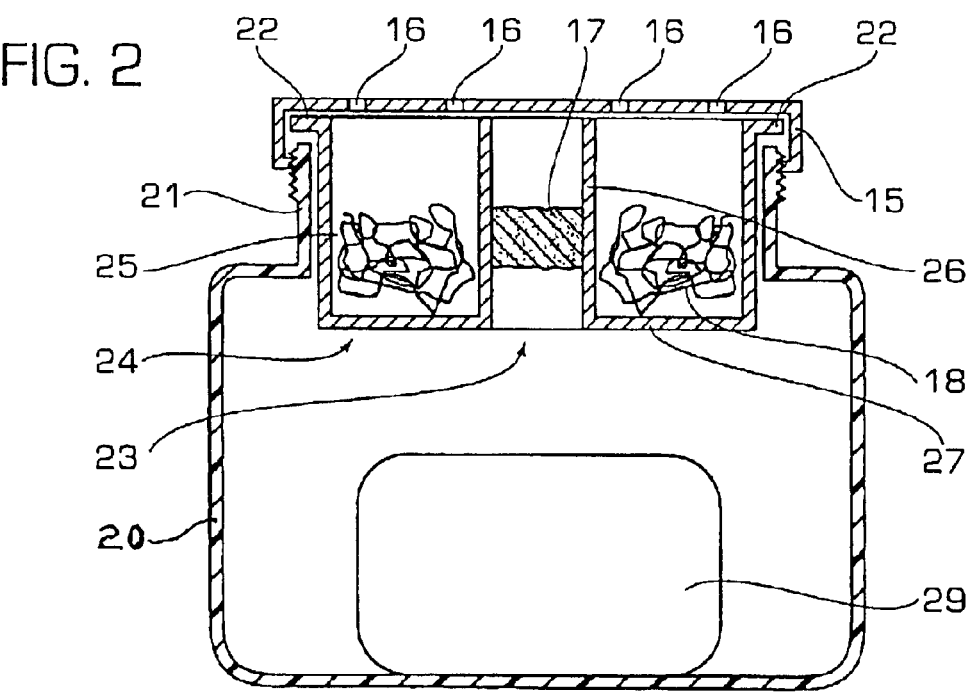
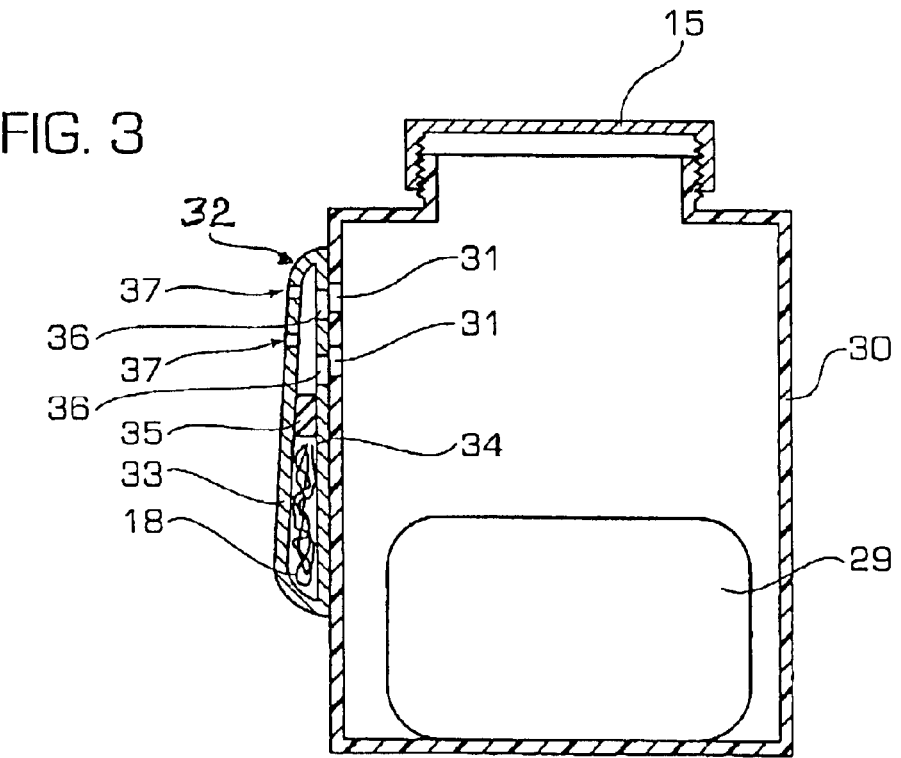

APPARATUS FOR PROVIDING AN ENVIRONMENT OF CONTROLLED WATER ACTIVITY FOR STORAGE OF NEMATODES

CROSS-REFERENCE

This application is a continuation of U.S. patent application Ser. No. 09/806,143, filed Mar. 28, 2001 (now U.S. Pat. No. 6,407,310). U.S. application Ser. No. 09/806,143 was the U.S. national phase of International patent application No. PCT/AU99/00829 filed Sep. 28, 1999.

TECHNICAL FIELD

This invention concerns containers which can be used for the storage of third stage infective juvenile entomopathogenic nematodes (often called "J3 nematodes") of the genera *Steinernema* (synonym Neoaplectana) and *Heterorhabditis* (synonym Chromonema). It is particularly useful for the storage of J3 nematodes which have been induced into a state of cryptobiosis—for example, as a consequence of the method disclosed in the specification of U.S. patent application Ser. No. 09/806,143. Long term storage of such cryptobiotic J3 nematodes requires a substantially constant, predetermined water activity in the storage container. However, the present invention can be used in other situations where an environment which has a substantially constant, predetermined water activity is necessary.

Because the present invention was developed for the optimal long term storage of J3 nematodes, that application of the invention is emphasized in this specification.

BACKGROUND TO THE INVENTION

Traditionally, samples of J3 entomopathogenic nematodes which have been reared in large quantities are stored—for transportation or for future use—in containers which are aerated. Aeration is essential if the nematodes are to survive, for they require oxygen (air) to be able to respire properly. Hence, some storage containers have positive ventilation provided by holes in the top or side walls of the container, and other containers use a membrane, or a panel, of a material through which air can permeate, to provide the necessary oxygen to the nematodes.

Aeration, however, is only one of the requirements for successful long term storage of cryptobiotic J3 nematodes. Another requirement is that the water activity of the storage environment must be maintained at substantially the required (pre-determined) value.

If a fixed amount of water is provided in the container in which the nematodes are to be stored, the aeration of the container will result in some water loss from the storage environment. With long term storage, this loss of water from the container can reduce the water activity within the container, so that the nematodes begin to dry out. Further loss of water from the container results in further desiccation of the J3 nematodes, which affects them adversely, and can lead to their death.

Clearly, it will be advantageous to maintain the water activity in the storage environment at the preferred or required value for successful long term storage—and this is one of the objectives of the present invention.

DISCLOSURE OF THE PRESENT INVENTION

To achieve the above-mentioned objective, the present invention utilises a water activity control attachment comprising a chamber in which the water activity can be controlled. This chamber is mounted on a container, with communication between the inside of the chamber and the inside of the container through at least one aperture in the chamber and at least one opening in the container.

Thus, according to the present invention, apparatus for providing an air-ventilated region of substantially constant pre-determined water activity comprises a container having at least one opening therein and a chamber adapted to be mounted on said container, said chamber having at least one aperture therein which is operatively connected with said opening, or with a respective opening in said container, whereby, when said apparatus is in use and an absorbent material which has been saturated with water or with a saturated salt solution is placed within said chamber, so that the water activity within said chamber is at said predetermined value, the interior of said container comprises a region which is maintained at said predetermined water activity value.

Note: In this specification, including the claims, directional terms (such as "upper", "lower", "top", "bottom", "vertical", "horizontal", and the like) will have their normal meaning when an embodiment of the invention is positioned as shown in the accompanying drawings.

In one realisation of the invention, the chamber attached to the container comprises a generally rigid tube which (a) is adapted to be fitted in an airtight manner in or over an opening in the container, so that on end of the tube is within the container; and (b) has its other end within a chamber which has at least one small aperture therein which connects the inside of the chamber to the outside air.

When the chamber is providing water activity control, this tube will preferably contain a plug of an air-permeable material, such as cotton wool, and the chamber will contain a water-absorbent material that has been saturated with water (or with a salt solution if a specific water activity is required within the storage container). For example, if a water activity of 0.97 is to be established, the water-absorbent material may contain a saturated solution of potassium sulphate.

An alternative form of the chamber of the invention has been designed to fit within, and be supported by, the neck of a wide-necked jar. The preferred form of this alternative realisation of the invention comprises:

a) an annular chamber adapted to fit within the neck region of the wide-necked jar, the outer diameter of the annular chamber being slightly less than the inner diameter of the neck of the jar; the chamber being open at its top and closed at its base, whereby the central portion of the annular chamber forms a tube which is coaxial with the neck of the chamber;

b) a flange extending horizontally outwardly from the top periphery of the chamber, the flange having dimensions such that the flange is adapted to be supported by the upper surface of the neck when the chamber is placed within the neck; and c) a cap adapted to fit over the neck, the cap having at least one small ventilation hole in it.

When this form of the invention is in use, a water-absorbent material which has been saturated with water or with a concentrated salt solution is placed within the annular chamber, and a plug of air-permeable material should be inserted into the tube at the centre of the chamber.

Another alternative form of the present invention has an attachment comprising a plastic envelope having a front face and a rear face, a layer of adhesive being applied over at least the region of the rear face which is adjacent to the edge thereof. The rear face has at least one aperture in it, in the upper region of this face. The front face of the envelope has at least one small aperture in it, also in the upper region thereof.

When this attachment is used to control the water activity of cryptobiotic J3 entomopathogenic nematodes stored in the associated container, the envelope is affixed, using the adhesive layer, to the wall (or to a wall) of the container, that wall having at least one opening in it, with the aperture (or apertures) in the rear face of the envelope being at least partially aligned with (that is, overlapping) the opening (or openings) in the container wall. When in use, the envelope will contain a water-absorbent material which has been saturated with water or with a saturated salt solution, and may also contain at least one flexible spacing member to ensure that the front and rear faces of the envelope are separated from each other and that the aperture(s) in the front face of the envelope does (do) not overlap the aperture (s) in the rear face of the envelope.

Embodiments of these forms of the invention will now be described, by way of example only, with reference to the accompanying drawings.

BRIEF DESCRIPTION OF THE DRAWINGS

FIG. 1 is partially schematic sectional view of a container, constructed in accordance with the present invention, being used to store cryptobiotic J3 nematodes.

FIG. 2 illustrates, also in the form of a partially schematic sectional view, a second embodiment of the present invention, being used to store cryptobiotic J3 nematodes.

FIG. 3 is a schematic sectional view of a third embodiment of the present invention, being used to store cryptobiotic J3 nematodes.

DETAILED DESCRIPTION OF THE ILLUSTRATED EMBODIMENTS

In the embodiment illustrated in FIG. 1 of the accompanying drawings, a container 10, having a large opening 11 in its upper surface, is closed by a screw cap 12. A tube 13 is sealed into an aperture which has been cut into the screw cap 12. If the opening 11 of the container 10 is normally closed by a rubber bung, the tube 13 would be an airtight fit in an aperture cut into that bung.

The lower end of the tube 13 is within the container 10. The upper end of the tube 13 extends into—and is sealed into—a cylindrical chamber 14, the upper wall of which comprises a screw cap 15. The screw cap 15 contains at least one ventilation hole 16 (several ventilation holes 16 are shown in FIG. 1). If the screw cap 15 is replaced with a suitable lid (which will always be the case if the chamber 14 is not cylindrical), that lid will be provided with at least one air hole (ventilation aperture) 16.

The chamber 14 contains water-saturated polyacrylamide gel particles 18 (or particles of another suitable water-absorbent material) around the lower region of that part of the tube 13 that is within the chamber 14, to maintain a water activity of 1.00 in the air within the chamber 14. If a saturated salt solution is used to saturate the polyacrylamide gel particles, a different required water activity will be established and maintained within the chamber 14 and—by transfer of air along the tube 13—within the container 10.

The use of a saturated salt solution enables the establishment of a selected or predetermined water activity of other than 1.00 within the chamber 14, and hence within the container 10.

The tube 13 contains a plug 17 of cotton wool, or other suitable material which permits transfer of air into and out of the container 10, but which prevents microbes and small bugs, dust particles and other particulate contaminant material from entering the container 10.

Variations of the arrangement illustrated in FIG. 1 of the accompanying drawings can be made to suit individual storage containers. For example, if the storage container should have a side opening instead of a top opening, the lower part of the tube 13 (that is, that part of the tube 13 that is below the base of the chamber 14) would be longer and would be bent so that the tube could enter the container 10 substantially horizontally, with the chamber 14 performing its normal function as a non-spill water reservoir.

A modified form of the FIG. 1 embodiment is illustrated in FIG. 2. In this drawing, a sample 29 of J3 entomopathogenic nematodes is shown stored within the container 20. The container 20 has a wide neck 21 which is closed by a lid or cap 15. The cap 15 may be screwed onto the neck 21 or it may be a snap-fit over the neck 21. As in the embodiment illustrated in FIG. 1, the cap 15 in FIG. 2 is provided with a number of small ventilation apertures 16. An annular chamber 24 is supported within the neck region of the container 20.

The annular chamber 24 has a substantially vertical outer side wall 25 and a substantially vertical inner side wall 26. The outer diameter of the side wall 25 is slightly less than the inner diameter of the neck 21. The walls 25 and 26 are joined by an annular web portion 27. The chamber 24 is open at its top and the inner side wall 26 forms a tube 23 which contains an air-permeable plug 17. A flange 22 extends outwardly, horizontally, from the top of the side wall 25 for a distance such that (a) the flange 22 overlaps the top surface of the neck 21, and (b) the outer diameter of the flange 22 is less than the inside diameter of the side wall of the cap 15. The annular chamber 24 contains a water-absorbent material 18 (such as polyacrylamide gel particles) saturated with water (or, optionally, with a saturated salt solution) to maintain the water activity of the air above the chamber 24, and thus within the container 20, at a value of 1.00 (or the value determined by the use of the salt solution).

The chamber 24 may be formed from any suitable material by moulding or by pressing.

The storage arrangement illustrated in FIG. 3 comprises of a container 30, with an airtight cap or lid 15. A sample 29 of cryptobiotic J3 nematodes with their support medium, at the required water activity, is within the container 30. The container 30 has a number of apertures 31 in its side wall (or in one of its side walls if the horizontal cross-section of the body of the container 30 is polygonal (for example, rectangular).

A plastic envelope 32, having a front face 33 and a rear face 34, contains (a) polyacrylamide gel particles or starch polyacrylamide gel particles 18, saturated with water or with a saturated salt solution, and (b) a flexible spacer member 35. The spacer member 35, which may conveniently be a strip of the material marketed under the trade mark "SCOTCHBRITE", ensures that the front and rear faces of the envelope do not come into contact with each other during the storage period. The rear face 34 is coated—at least over a region adjacent to the edge of the rear face—with an adhesive material which enables the rear face to be stuck onto the container 30. As shown in FIG. 3, apertures 36 in the rear face 34 of the envelope substantially coincide with (that is, at least partially overlap) the apertures 31 in the container 30. The front face 33 of the envelope has a plurality of small apertures 37 in it, which permit air to enter the envelope and pass through the apertures 36 and 31, to provide a supply of oxygen for the nematodes in the sample 29 while maintaining a water activity of 1.00 (or the value established by the saturated salt solution) within the container 30.

It will be apparent to persons of skill in this field that the above-described embodiments of the present invention are illustrative only of the invention, and that variations to and modifications of the described embodiments may be made without departing from the present inventive concept, as defined by the claims.

We claim:

1. Apparatus for providing an air-ventilated region of constant predetermined water activity value, said apparatus comprising a container and a chamber positioned outside said container, characterized in that:
    a) said chamber has an opening therein which is closed by a lid;
    b) said lid has at least one small aperture therein to vent said chamber to the atmosphere;
    c) said container has an opening therein, to provide access to the interior of said container, and a cover positioned over said opening;
    d) a rigid tube passes through a wall of said chamber and also through said cover, the outer surface of said tube being an airtight fit with said wall of said chamber and with said cover;
    whereby (1) said tube connects the inside of said chamber with the inside of said container, and wherein (2) an absorbent material saturated with water or with a saturated salt solution is within said chamber, so that the water activity within said chamber is at said constant predetermined water activity value, and the interior of said container comprises a region which is maintained at said constant predetermined water activity value.

2. Apparatus as defined in claim 1, including a plug of an air-permeable material within said tube.

3. Apparatus for providing an air-ventilated region of constant predetermined water activity value, said apparatus comprising a container and a chamber, characterized in that:
    a) said container is a jar with a single opening in the top thereof, said opening being formed as a circular neck;
    b) said chamber is an annular chamber having a tubular outer wall and a tubular inner wall, said outer wall and said inner wall being connected at the base of said chamber by an annular web member; said chamber being open at the top thereof;
    c) an annular flange extends horizontally outwardly from the top of said outer wall, said flange having a diameter which is substantially the same as the outer diameter of said neck; said outer wall having an outer diameter which is slightly smaller than the inner diameter of said neck; whereby said chamber fits within said neck with said flange resting on the top of said neck; and
    d) a cap fits over said flange and said neck; said cap having at least one small aperture therein to vent said chamber and said container to the atmosphere;
    whereby (1) said tubular inner wall provides a connection between the inside of said chamber and the inside of said container, and wherein (2) an absorbent material saturated with water or with a saturated salt solution is within said chamber, so that the water activity within said chamber is at said constant predetermined water activity value, and the interior of said container comprises a region which is maintained at said constant predetermined water activity value.

4. Apparatus as defined in claim 3, in which said neck is threaded on the outer side surface thereof and said cap has a side wall with at least one projection therefrom to enable said cap to be screwed onto said neck.

5. Apparatus as defined in claim 3, including a plug of an air-permeable material within said tubular inner wall.

6. Apparatus for providing an air-ventilated region of constant predetermined water activity value, said apparatus comprising a container and a chamber, characterized in that:
    a) said container has a side wall and at least one opening is formed in said side wall;
    b) said chamber comprises a plastic envelope having a front face and a rear face; said front face has at least one aperture therein in the upper region of said front face; said rear face has at least one aperture therein in the upper region of said rear face;
    c) said rear face is bonded to said side wall at the peripheral region of said rear face by a layer of adhesive; said at least one aperture in said rear face being aligned with said at least one opening in said wall of said container;
    whereby (1) said aligned apertures provide a connection between the inside of said chamber and the inside of said container, and wherein (2) an absorbent material saturated with water or with a saturated salt solution is within said chamber, so that the water activity within said chamber is at said constant predetermined water activity value, and the interior of said container comprises a region which is maintained at said constant predetermined water activity value.

7. Apparatus as defined in claim 6, including at least one flexible spacing member within said envelope.

8. Apparatus for providing an air-ventilated region of constant predetermined water activity value, said apparatus comprising a container and a chamber, characterized in that:
    a) said container has a plurality of side walls and at least one opening is formed in one of said side walls;
    b) said chamber comprises a plastic envelope having a front face and a rear face; said front face has at least one aperture therein in the upper region of said front face; said rear face has at least one aperture therein in the upper region of said rear face;
    c) said rear face is bonded to said one of said side walls at the peripheral region of said rear face by a layer of adhesive; said at least one aperture in said rear face being aligned with said at least one opening in said one of said side walls of said container;
    whereby (1) said aligned apertures provide a connection between the inside of said chamber and the inside of said container, and wherein (2) an absorbent material saturated with water or with a saturated salt solution is within said chamber, so that the water activity within said chamber is at said constant predetermined water activity value, and the interior of said container comprises a region which is maintained at said constant predetermined water activity value.

9. Apparatus as defined in claim 8, including at least one flexible spacing member within said envelope.

* * * * *